United States Patent [19]

Arai et al.

[11] Patent Number: 5,059,526

[45] Date of Patent: Oct. 22, 1991

[54] DRY MULTILAYER ANALYTICAL ELEMENT FOR ANALYSIS OF ENZYMES OR TRIGLYCERIDES

[75] Inventors: Kazumi Arai; Mario Kobayashi; Kenichiro Okaniwa, all of Hino, Japan

[73] Assignee: Konishiroku Photo Industry Co., Ltd., Tokyo, Japan

[21] Appl. No.: 494,931

[22] Filed: Mar. 14, 1990

Related U.S. Application Data

[63] Continuation of Ser. No. 14,142, Feb. 12, 1987, abandoned, which is a continuation of Ser. No. 527,680, Aug. 29, 1983, abandoned.

[30] Foreign Application Priority Data

Sep. 6, 1982 [JP] Japan .................. 67-155701
Nov. 12, 1982 [JP] Japan .................. 67-198446

[51] Int. Cl.$^5$ .................. C12Q 1/50; C12Q 1/44; C12Q 1/26; G01N 31/22
[52] U.S. Cl. .................. 435/17; 422/56; 422/61; 424/7.1; 435/18; 435/19; 435/22; 435/25; 435/26; 435/805
[58] Field of Search .................. 435/17, 18, 19, 22, 435/25, 26, 805; 422/56, 57, 58, 60, 61; 424/7.1; 436/514

[56] References Cited

U.S. PATENT DOCUMENTS

| | | | |
|---|---|---|---|
| 3,992,158 | 11/1976 | Przybylowicz et al. | 435/14 |
| 4,042,335 | 8/1977 | Clement | 435/14 |
| 4,066,403 | 1/1978 | Bruschi | 436/170 |
| 4,097,338 | 6/1978 | Konttinen et al. | 435/26 |
| 4,144,306 | 3/1979 | Figueras | 435/14 |
| 4,166,093 | 8/1979 | Smith-Lewis et al. | 435/14 |
| 4,503,145 | 3/1985 | Katsuyama et al. | 435/16 |

*Primary Examiner*—David M. Naff
*Attorney, Agent, or Firm*—Frishauf, Holtz, Goodman & Woodward

[57] ABSTRACT

A stable dry multi-layer analytical element for enzyme or triglyceride analysis in a fluid sample is prepared containing first and second layers on a support. The first layer contains a tetrazolium salt as a dye forming precursor. The second layer is adjacent the first layer and contains an electron-transmitting agent. Either layer contains a co-enzyme in oxidized form and either layer contains a reagent containing an enzyme substrate, enzyme or co-enzyme other than the oxidized co-enzyme. The analytical element has improved storage stability and low fog density before and after storage.

28 Claims, No Drawings

DRY MULTILAYER ANALYTICAL ELEMENT FOR ANALYSIS OF ENZYMES OR TRIGLYCERIDES

This application is a continuation of application Ser. No. 07/014,142, filed Feb. 12, 1987 which is a continuation of Ser. No. 06/227,680 filed Aug. 29, 1983 both now abandoned.

This invention relates to an analytical element, particularly to an analytical element for analysis of a specific component in a fluid. More particularly, it pertains to a dry system analytical element for analysis of a specific component in a biological fluid sample through a reduction type co-enzyme.

In the prior art, there have been developed a large number of methods for analysis of specific components in fluid samples. These methods may be classified broadly into the two kinds of systems, namely the reaction system in which the reaction is conducted in a solution and the reaction system in which the reaction is conducted in a solid phase carrier. The analytical reaction in the solution reaction system (hereinafter referred to as wet chemistry) includes a large number of procedures, varying widely from an analytical procedure of the so called manual method in which no machine is used at all to automatic analytical instrument. Particularly, in the field of clinical chemistry, the progress of automatic analyzer can markedly be seen, and various automatic quantitative analyzers for clinical testing have been introduced in recent years into clinical test rooms in hospitals.

However, in the above method, the reaction is carried out basically in the form of an aqueous solution, and therefore various problems are involved. For example, since a large amount of water, particularly purified pure water or distilled water is necessary, an increased consumption of energy may be caused. In addition, various automatic analyzers are themselves very expensive and great skills are required for their operations, thus necessitating enormous amounts of time and labor, and their waste liquors will necessarily cause environmental pollution.

On the other hand, analytical methods utilizing analytical reactions in solid phase (hereinafter referred to as dry chemistry) have also been used widely, and these are practiced in the form filter paper or other materials impregnated with a reagent.

The above filter paper is prepared by impregnating a water-absorptive fibrous carrier such as filter with a reagent solution, followed by drying, as disclosed in U.S. Pat. No. 3,050,373 or 3,061,523. These are called generally as analytical test papers or merely as test strips, and a fluid sample is added dropwise on a test strip, or a test strip is dipped in a fluid sample, and the color change or density change of the test strip is measured by judgement with naked eyes or by means of a reflection densitometer, to determine concentration level of a specific component in the fluid sample.

These test strips are useful, since they are easy in handling and can give directly the result of test, but its usefulness is still in the field of semi-quantitative analysis or qualitative analysis due to its constitution.

On the other hand, as contrasted to the analytical methods of the prior art as described above, a multilayer analytical element is known, which element utilizes dry chemistry simple in operation and yet has quantitative characteristic. For example, such multilayer elements are disclosed in Japanese Patent Publication No.21677/1978, Japanese Provisional Patent Publication Nos.164356/1980,. 125847/1982, 197466/1982 and 90167/1983.

According to the elements as disclosed in these specifications, all the reagents to be used for an analytical reaction are contained in one sheet of an analytical element, and a certain volume of serum or whole blood is added dropwise onto the above element, and after incubation at a constant temperature for a predetermined period of time, measurement of reflected density is conducted from the support side, from which reflected density the density of a material can be determined.

The above method has an analytical precision which is revolutionarily higher as compared with that of a test strip type method of the prior art, and also has a performance more than equal to that of wet chemistry without previous preparation of a reagent.

However, such an analytical element utilizing dry chemistry is provided primarily for use in analysis of low molecular weight compounds, and analysis is performed mostly according to the end point assay without any development in the prior art of assaying of a high molecular substance, particularly activity of an enzyme utilizing the rate assay.

In particular, the method of assaying a component in a fluid sample through increase or decrease of a reduction type co-enzyme, namely reduction type nicotinamide adenine dinucleotide or reduction type nicotinamide adenine dinucleotidric acid, has been known to be widely applicable and useful.

These reduction type co-enzymes have been applied in wet chemistry, and one known method comprises converting a specific component in a sample according to a desired intermediary reaction route to a certain product, which is then led to a reaction for decreasing a reduction type co-enzyme, and detecting the reduction type co-enzyme at the UV-region thereof according to the rate assay, or alternatively another method comprises transmitting the change in a reduction type co-enzyme through an electron transmitting agent to a color forming precursor, thereby forming a dye, and quantifying the density of the color according to colorimetry.

The former method, which is generally employed in wet chemistry, involves some vital problems in application for an analytical element of dry chemistry. First, the change in a reduction type co-enzyme to be assayed is required to measure the absorption in the UV-region at 340 nm and its spectral absorption coefficient is also known to be markedly small. Therefore, it is necessary to measure a minute change at the UV-region, and the reflective light measurement required on account of the structure of the analytical element will demand a measuring instrument of higher performance, namely a markedly expensive measuring instrument. Furthermore, difficulties are encountered in use of all materials having no absorption around 340 nm, which is required because of the requisite measurement at the UV-region.

The latter method is not only by far advantageous in that it is capable of quantifying a dye formed through an electron transmitting agent according to colorimetry at the visible region than the former method but also very advantageous in that both of the rate assay and the end point assay are available.

In spite of such advantageous aspects, the latter method has not frequently been applied in wet chemistry. This is not only because of the critical drawback that co-presence of both of the aforesaid electron transmitting agent and the dye-forming precursor in a solution system will lower stabilities of these substances to induce formation of undesirable dyes, but also because of lowering in precision during mixing of both and insolubility of most of the dyes derived from dye-forming precursors in water, whereby the dyes are precipitated in an aqueous solution to cause such problems as lowering in precision or deterioration in reproducibility based on such precipitates.

Thus, when the latter method is applied merely for a multi-layer analytical element, it can evidently be seen that not only usefulness possessed inherently by a multi-layer analytical element can not be exhibited, but moreover no sufficiently satisfactory result with respect to stability of a reagent and assay precision can be obtained.

Accordingly, it would be very desirable to develop an analytical element for which the latter method is applied, while maintaining the usefulness as a multi-layer analytical element.

An object of the present invention is, therefore, to provide a dry system analytical element for simple analysis of a specific component in a biological fluid sample by use of a reduction type co-enzyme, which is excellent in stability and assay precision.

That is, the analytical element of this invention is an analytical element for analysis of a specific component in a fluid sample having provided successively essential layers of at least one receptor layer and at least one spreading layer on a support, which comprises containing at least one kind of electron transmitting agent, at least one kind of dye-forming precursor, at least one oxidation type co-enzyme and at least one kind of reagent capable of converting said oxidation type co-enzyme to a reduction type co-enzyme through said specific component (hereinafter called as the reagent according to this invention).

The electron transmitting agent according to this invention acts to be reduced in the presence of a reduction type co-enzyme, which is formed between at least one kind of the reagent according to this invention and an oxidation type co-enzyme through the presence of a specific component in a biological fluid sample, said electron transmitting agent reduced further acting to reduce a dye-forming precursor thereby to form a dye having an absorption at the visible region.

As the specific components which can be assayed in a fluid sample in this invention, there may be included lactate dehydrogenase (LDH), glutamate-oxaloacetate transaminase (GOT), glutamate-piruvate transaminase (GPT), amylase (AMY), creatine phosphokinase (CPK) and triglycerides (TG).

The reagent according to this invention refers primarily to a substrate or an enzyme, including sometimes also co-enzymes. These reagents may be suitably selected depending on the specific component in a biological fluid sample to be assayed. For example, lactic acid may be used in case of assay of LDH, aspartic acid; α-ketoglutaric acid and glutamate dehydrogenase (GlDH) in case of GOT; alanine, α-ketoglutaric acid and glutamate dehydrogenase in case of GPT; maltopentose, orthophosphoric acid, β-phosphoglucomutase (β-PGM), glucose oxidase (GOD) and maltose phosphorylase in case of AMY; creatine, adenosine triphosphoic acid (ATP), hexokinase (HK) and glucose-6-phosphate dehydrogenase (G-6-PDH) in case of CPK; and lipoprotein lipase (LPL), glycerokinase (GK), glycerophosphate dehydrogenase (GPDH) and adenosine triphosphoric acid (ATP) in case of TG.

The oxidation type co-enzyme according to this invention refers to oxidation type nicotinamide adenine dinucleotide (NAD+) and oxidation type nicotinamide adenine dinucleotide phosphoric acid (NADP+), and the like. The reduction type co-enzyme refers to a reduction type of the oxidation type co-enzyme. The reduction type of NAD+ is NADH and that of NADP+ is NADPH.

In the following are set forth the reaction schemes to form reduction type co-enzymes through the reaction between at least one reagent according to this invention and an oxidation type co-enzyme in the presence of a specific component in a biological fluid sample according to this invention.

LDH

Lactic acid + NAD+ $\xrightarrow{\text{LDH}}$ Piruvic acid + NADH

GOT

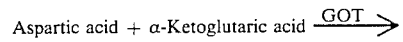
Aspartic acid + α-Ketoglutaric acid $\xrightarrow{\text{GOT}}$

Oxaloacetic acid + Glutamic acid

Glutamic acid + NAD+ $\xrightarrow{\text{GlDH}}$ α-Ketoglutaric acid + NADH

GPT

Alanine + α-Ketoglutaric acid $\xrightarrow{\text{GPT}}$

Piruvic acid + Glutamic acid

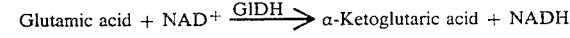
Glutamic acid + NAD+ $\xrightarrow{\text{GlDH}}$ α-Ketoglutaric acid + NADH

AMY

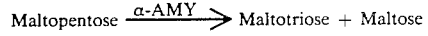
Maltopentose $\xrightarrow{\alpha\text{-AMY}}$ Maltotriose + Maltose

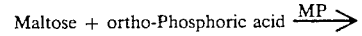
Maltose + ortho-Phosphoric acid $\xrightarrow{\text{MP}}$

Glucose + β-D-glucose-1-phosphate

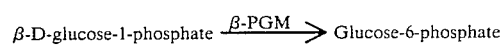
β-D-glucose-1-phosphate $\xrightarrow{\beta\text{-PGM}}$ Glucose-6-phosphate

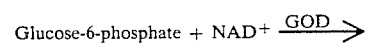
Glucose-6-phosphate + NAD+ $\xrightarrow{\text{GOD}}$

6-Phosphogluconic acid + NADH

CPK

Creatine + ATP $\xrightarrow{\text{CPK}}$ Creatinephosphoric acid + ADP

Glucose + ATP $\xrightarrow{\text{HK}}$ ADP + Glucose-6-phosphoric acid

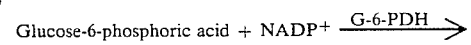
Glucose-6-phosphoric acid + NADP+ $\xrightarrow{\text{G-6-PDH}}$

6-Phosphogluconic acid + NADPH

TG

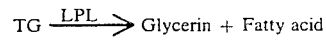
TG $\xrightarrow{\text{LPL}}$ Glycerin + Fatty acid

-continued

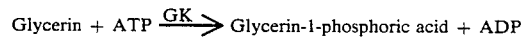

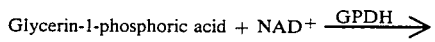

Dihydroxyacetone phosphoric acid + NADH

As the electron transmitting agent to be used in the present invention, there may be included N-methylphenazine methosulfates (e.g. N-methylphnazinemethosulfate, 1-methoxy-N-methylphenazinemethosulfate, etc.), Meldra Blue, Methylene Blue and diaphorase. Preferably, N-methylphenzaine methosulfates may be employed.

On the other hand, as the dye-forming precursor according to this invention, there may be generally employed tetrazolium salts. Most of the above tetrazolium salts to be used in the present invention will become difficultly soluble or insoluble in water after formation of dyes, and therefore difficultly applicable generally for wet chemistry. However, the dyes formed are diffusion resistant to prevent undesirable ringing to improve quantitative precision of assay, and they can preferably be used with respect to this point.

As the useful tetrazolium salts in this invention, there may be included, for example, 3,3'-(3,3'-dimethoxy-4,4'-biphenylene)-bis [2-(p-nitrophenyl)-5-phenyltetrazoliumchloride] (NBT), 3,3'-(3,3'-dimethoxy-4,4'-biphenylene)bis[2,5-diphenyltetrazoliumchloride](BT), 3-(4,4,5'-dimethyl-triazolyl 2)-2,4-diphenyltetrazolium bromide (MTT), 2-(p-iodophenyl)-3-(p-nitrophenyl)-5-phenyltetrazolium chloride (INT), 2,2',5,5'-tetra-(p-nitrophenyl)-3, 3'-(3-dimethoxy-4-diphenylene)-ditetrsazolium chloride (TNBT), 2,3,5-triphenyltetrazolium chloride (TT) and 3,3'-(4,4'-biphenylene)-bis[2,5diphenyltetrazolium chloride](NT).

The reagent and the oxidation type co-enzyme to be contained in the analytical element of this invention may be contained in either one of at least one receptor layer and at least one spreading layer. Also each of the electron transmitting agent and the dye-forming precursor may be contained in either of at least one receptor layer and at least one spreading layer. However, prior to application of a fluid sample, it is necessary that these electron transmitting agent and dye-forming precursor should be contained under the condition unreactive with each other lest undesirable dye should be formed. Therefore, it is preferred that the electron transmitting agent and the dye-forming precursor should be contained in different layers. Alternatively, even when contained in the same layer, these electron transmitting agent and dye-forming precursor should be contained as particles separate from each other.

In an analytical element, wherein the electron transmitting agent and the dye-forming precursor are contained in different layers, either one or more layer contains the electron transmitting agent and either one or more layer containing no electron transmitting agent contains the dye-forming precursor, the electron transmitting agent may be contained in either the spreading layer and the dye-forming precursor in the receptor layer, or vice versa, but preferably according to the former state. In this case, it is more preferable to have a layer containing none of these electron transmitting agent and dye-forming precursor interposed between the spreading layer containing the electron transmitting agent and the receptor layer containing the dye-forming precursor.

When the electron transmitting agent and the dye-forming precursor are to be contained in different layers, these incorporating layers may be provided according to the method in which the electron transmitting agent or the dye-forming precursor is dissolved in an aqueous binder solution, more specifically dissolved in a solution, followed by dissolution of the resultant solution in a binder dissolved in water, and the solution obtained is provided by coating.

When the electron transmitting agent and the dye-forming precursor are to be contained as particles separated from each other in the same layer, each of these electron transmitting agent and the dye-forming precursor should preferably have particle sizes of 0.1 $\mu$ or more.

Further, also in case when the electron transmitting agent and the dye-forming precursor are contained in different layers, these electron transmitting agent and/or dye-forming precursor can be made into particulate shapes.

As the method for providing a layer containing the electron transmitting agent and the dye-forming precursor as particles, there may be employed the method in which previously micropulverized electron transmitting agent and dye-forming precursor are suspended in an organic solvent, the resultant suspension is added into a binder dissolved in the same organic solvent and the homogeneous dispersion obtained is provided by coating; the method in which each of the electron transmitting agent and the dye-forming precursor is suspended in an organic solvent to be micropulverized therein, added to a binder dissolved in the same solvent to be homogeneously dispersed therein and the resultant dispersion is coated; or the method wherein the electron transmitting agent and a dye-forming precursor are micropulverized in an organic solvent containing a binder, followed by homogenization and coating.

When the spreading layer is constituted of a fibrous porous material such as filter paper, it is also possible to use the method in which the electron transmitting agent and the dye-forming precursor may be added to an organic solvent containing a binder, and then a porous material is added to be homogeneously dispersed therein, followed by coating of the resultant dispersion.

The electron transmitting agent according to this invention may be contained in the analytical element of this invention in an amount, which may differ depending on the content of the aforesaid specific component, but generally ranges from 1 mg/m$^2$ to lg/m$^2$, preferably from 10 to 500 mg/m$^2$. The content of the dye-forming precursor in the analytical element of this invention may be generally in the range from 10 mg/m$^2$ to 10 g/m$^2$, preferably from 50 mg/m$^2$ to 3 g/m$^2$. Further, the content of the oxidation type co-enzyme according to this invention in the analytical element is generally in the range from 10 mg/m$^2$ to 50 g/m$^2$, preferably from 50 mg/m$^2$ to 10 g/m$^2$. On the other hand, the total amount of the reagent according to this invention cannot be equal depending on the kind of the reagent employed, but it is contained generally in an amount ranging from 10 mg/m$^2$ to 100 g/m$^2$.

The binder to be used for formation of a layer containing the above electron transmitting agent and a layer containing the dye-forming precursor is not particularly limited, but the binder for a layer containing the dye-forming precursor should preferably be a gelatin derivative. The method for forming the layer is not particularly limited. When the electron transmitting agent and the dye-forming precursor are to be contained in the same layer as particles from each other, the binder in the layer containing these should preferably be a hydrophobic binder so that it may not dissolve these therein.

The analytical element thus constituted of this invention is improved to a great extent in storage stability of the element, including the fog density of the analytical element, thus enabling achievement of a high distinguishing ability.

The spreading layer according to this invention has the function (1) to distribute a constant volume of a fluid sample uniformly to a constant volume per unit area through the receptor layer. Moreover, it is preferably provided with the function as described in Japanese Patent Publication No. 21677/1978, namely (2) to remove substances or factors which interfere with the analytical reactions in the fluid sample and/or (3) to effect a background action which reflects the measured light transmitted through the support during spectrophotometric analysis. Accordingly, the spreading layer according to this invention can be made into a layer having only the above function (1), or a layer having the function (2) and/or (3) in addition to (1), or alternatively, a plurality of functions including (1) may be suitably separated and different layers having respective functions can be used. Further, it is also possible to use a layer having two of the functions (1), (2) and (3) and a layer having the other one remaining function. For example, there may be mentioned a spreading layer of a non-fibrous porous medium called as the brush polymer comprising titanium dioxide and cellulose diacetate as disclosed in the above Japanese Patent Publication No.21677/1978, and the spreading layers of fibrous structure as disclosed in Japanese Provisional Patent Publications No.24576/1981, No.125847/1982 and No. 197466/1982. In particular, the above spreading layer of fibrous structure is particularly useful as a material enabling rapid delivery of blood cell portion, and further useful for spreading delivery of macromolecules such as enzymes which is one objects of this invention. The spreading layer in the analytical element of this invention may have a film thickness, which should be determined depending on its void volume, but preferably about 100 to about 500 microns, more preferably about 150 to 350 microns. Also, the void volume may preferably be about 20 to about 85 %.

The receptor layer according to this invention is provided for the purpose of being a site where a dye-forming precursor is changed within a receptor layer, or at least the dye changed from the dye-forming precursor is received and detected as the spectrophotometrically observed quantity, when the specific substance in a fluid sample converts a dye-forming precursor into a dye by the selected reaction finally through the electron transmitting agent. Various reagents and additives may be added within this purpose.

As other additives, it is also possible to add various additives such as preservatives, buffering agent, surfactants, etc., if desired.

Particularly, surfactants may be used effectively for the purpose of controlling the permeation speed of a fluid sample when applied to the element of the present invention, and other purposes.

As useful surfactants, there may be employed all surfactants of either ionic (anionic or cationic) or nonionic, but preferably nonionic surfactants are more effective. Examples of nonionic surfactants are polyalkylene glycol derivatives of alkyl-substituted phenols such as 2,5-di-t-butylphenoxy polyethyleneglycol, p-octylphenoxy polyethyleneglycol, p-iso-nonylphenoxy polyethyleneglycol, and polyalkyleneglycol esters of higher fatty acids. These surfactants have the effect of controlling the permeation speed of a fluid sample into the receptor layer, simultaneously with the effect of inhibiting generation of undesirable "chromatography phenomenon".

The above surfactant may be employed in an amount which can be widely varied, but generally in an amount of 10 to 0.005 % by weight based on the weight of a coating solution, preferably 6 to 0.05 % by weight.

The aforesaid support according to the analytical element of the present invention (hereinafter abbreviated as the support according to the present invention) may be any kind of support, so long as it is impervious to liquids and light-transmissive. For example, various polymeric materials such as cellulose acetate, polyethylene terephthalate, polycarbonate or polystyrene are suitable for the purpose of use. Further, not only the above polymers but also inorganic materials such as glass may also be similarly available. The support according to this invention may have a thickness which can freely be selected, but preferably in the range from about 50 microns to about 250 microns. The one side surface on the observation side of the support according to this invention may also be freely worked depending on the purpose intended. Further, a light transmissive undercoating layer may also be used, if desired, on the side of the support where a reagent layer is to be laminated to improve the adhesion between the reagent layer and the support.

The analytical element of this invention can be made to constitute the analytical element in conformity with the object of the present invention by combining optionally with reflection layer, undercoating layer as disclosed in U.S. Pat. No. 3,992,158, radiation blocking layer as disclosed in U.S. Pat. No. 4,042,335, barrier layer as disclosed in U.S. Pat. No. 4,066,403, migration inhibition layer as disclosed in U.S. Pat. No.4,166,093 scintillation layer as disclosed in U.S. Pat. No. 4,127,499, scavenging layer as disclosed in Japanese Provisional Patent Publication No. 90859/1980 and destructive pod-like member as disclosed in U.S. Pat. No. 4,110,079, and the like.

Various layers of these analytical elements can be provided by successive coating to desired thicknesses, in accordance with the desired constitution, on the support according to this invention by use of the known method suitably selected such as the slide hopper coating method, the extrusion coating method and the dipping coating method.

By use of the analytical element of this invention, the quantity of a specific component in a fluid sample can be assayed according to the rate assay or the end point assay by reflection spectrophotometry from the support side according to this invention. From the assayed value thus obtained, the quantity of the specific component can be determined by referring to the calibration curve previously prepared.

A fluid sample to be applied to the analytical element of this invention may be used in an amount as desired, but preferably in an amount of about 5 $\mu l$ to about 50 $\mu l$ more preferably about 5 $\mu l$ to about 20 $\mu l$. Usually, it is preferred to use about 10 $\mu l$ of a fluid sample.

The analytical element of this invention can be applied for analysis of any of whole blood, serum and plasma without any inconvenience. Further, it is applicable without inconvenience for other body fluids such as urine, lymph, cerebospinal fluid, etc. When whole blood is to be employed, it is possible to provide the above-mentioned radiation blocking layer or other reflection layers, in order to avoid interference of blood cells with the radiation for detection, if desired.

The analytical reaction to be used for the analytical element of this invention can be determined as desired depending on its purpose, and it is useful in, for example, the field of clinical chemistry, particularly for analysis of a component in blood or urine.

As described in detail above, according to the analytical element of this invention, since the electron transmitting agent and the dye-forming precursor could be contained in the constituent layers under the state unable to react with each other until a liquid sample is applied to the analytical element, the reagent can be improved in storability and stability, with decreased fog density as well as excellent color forming property. Moreover, there is observed substantially no generation of ununiform density or chromatograph phenomenon. Accordingly, the analytical element of this invention can be used in high precision dry system quantative analysis of a component in a fluid sample, particularly a biological fluid sample, simply and rapidly by means of a conventional spectrophotometer, and therefore very advantageous in practical application.

This invention is further illustrated by referring to the following Examples, by which the embodiments of this invention are not limited at all.

EXAMPLE 1

(1) Preparation of Analytical element—1 of this invention

A. Preparation of coating solutions (a) In 150 ml of distilled water were dissolved 25 g of gelatin, 3.8 g of oxidation type nicotinamide adenine dinucleotide (NAD$^+$), 0.5 g of Triton X-100 (trade name, produced by Rohm & Haas Co.), 5 g of lithium lactate, 3.9 g of Tris-hydroxymethylaminomethane, 2.3 g of HCl-Trishydroxymethylaminomethane and 0.2 g of 1,2-bis(vinylsulfonyl)ethane, to provide a coating solution for receptor layer.

(b) A liquid of 100 ml of xylene to which 68 mg of 1-methoxy-N-methylphenazine methosulfate (MeO·PMS) was added and a liquid of 100 ml of xylene to which 820 mg of NBT was added were prepared separately, and MeO·PMS and NBT were each dispersed in minute particles in xylene with addition of 70 ml of glass beads by means of a sand gainder, followed by removal of the glass beads by filtration, to provide each xylene dispersion. Further, a xylene solution of 13 g of a styrene-glycidyl methacrylate copolymer [copolymeric ratio: 9 : 1 (weight ratio)] and 9 g of Triton X -100 dissolved in 300 ml of xylene was prepared, and the above two kinds of xylene dispersions and the xylene solution were mixed. Into the resultant mixture was added 91 g of a powdery filter paper C [produced by Toyo Roshi Co., 300 mesh or finer], followed by thorough stirring, to provide a coating solution for spreading layer.

B. Preparation of analytical element:

On a transparent polyethyleneterephthalate support applied with subbing of a film thickness of about 180 microns, the layers having the following compositions were successively coated by use of the above coating solutions (a) and (b) to prepare an analytical element—1 of this invention.

(a) Receptor layer: A layer containing the following:

| | |
|---|---|
| Gelatin | 25 g/m$^2$ |
| Lithium lactate | 5 g/m$^2$ |
| NAD$^+$ | 3.8 g/m$^2$ |
| Triton X-100 | 0.5 g/m$^2$ |
| Tris-hydroxymethylaminomethane | 3.9 g/m$^2$ |
| HCl-Tris-hydroxymethylaminomethane | 2.3 g/m$^2$ |
| 1,2-bis(vinylsulfonyl)ethane | 0.2 g/m$^2$ |

(b) Spreading layer: A layer containing the following:

| | |
|---|---|
| Powdery filter paper C | 91 g/m$^2$ |
| Styrene-glycidylmethacrylate (9:1) copolymer | 13 g/m$^2$ |
| MeO.PMS | 68 mg/m$^2$ |
| NBT | 820 mg/m$^2$ |
| Triton X-100 | 9 g/m$^2$ |

(2) Preparation of Analytical element—2 of this invention:

A. Preparation of coating solutions:

(a) A liquid of 50 ml of xylene to which 68 mg of MeO·PMS was added, a liquid of 50 ml of xylene to which 820 mg of NBT was added and a liquid of 100 ml of xylene to which 10 g of lithium lactate, 3.8 g of NAD$^+$, 3.9 g of Tris-hydroxymethylaminomethane and 2.3 g of HCl-Tris-hydroxymethylaminomethane were added were separately prepared, and the respective reagents were dispersed in minute particles in xylene with addition of 70 ml of glass beads to 100 ml of each liquid by means of a sand grinder, followed by separation of the beads by filtration, to provide respective xylene dispersions. Further, a xylene solution was prepared by adding 10 g of a styrene-methacrylate copolymer [copolymeric ratio 9:1 (weight ratio)]and 0.5 g of Triton X-100, and mixed with the above three kinds of xylene dispersions to provide a coating solution for receptor layer.

(b) A xylene solution was prepared by adding 13 g of a styrene-glycidyl methacrylate copolymer [copolymeric ratio 9:1 (weight ratio)]and 9 g of Triton X-100 to 300 ml of xylene, 9 g of a powdery filter paper C was added to the solution and the resultant mixture was stirred well to provide a coating solution for spreading layer.

B. Preparation of analytical element:

On a transparent polyethyleneterephthalate support applied with subbing of a film thickness of about 180 microns, the layers having the following compositions were successively coated by use of the above coating solutions (a) and (b) to prepare an analytical element of - 2 of this invention.

(a) Receptor layer: A layer containing the following:

| | |
|---|---|
| Styrene-Glycidyl methacrylate (9:1) copolymer | 10 g/m$^2$ |
| MeO.PMS | 68 mg/m$^2$ |
| NBT | 820 mg/m$^2$ |

-continued

| | |
|---|---|
| Lithium lactate | 10 g/m² |
| NAD+ | 3.8 g/m² |
| Tris-hydroxymethylaminomethane | 3.9 g/m² |
| HCl-Tris-hydroxymethylaminomethane | 2.3 g/m² |
| Triton X-100 | 0.5 g/m² |

(b) Spreading layer: A layer containing the following:

| | |
|---|---|
| Powdery filter paper C | 91 g/m² |
| Styrene-glycidylmethacrylate (9:1) copolymer | 13 g/m² |
| Triton X-100 | 9 g/m² |

(3) Preparation of Analytical element—3 of this invention

A. Preparation of coating solutions ($a_1$) In 150 ml of distilled water were dissolved 25 g of gelatin, 3.8 g of NAD+, 820 mg of NBT, 10 g of lithium lactate, 3.9 g of Tris-hydroxymethylaminomethane, 2.3 g of HCl-Tris-hydroxymethylaminomethane, 0.5 g of Triton X-100 and 0.4 g of 1,2-bis(vinylsulfonyl)ethane, to provide a coating solution for a first receptor layer.

($a_2$) To 50 ml of toluene was added 72 mg of MeO·PMS, and MeO·PMS was dispersed in minute particles in toluene with addition of 35 ml of glass beads by means of a sand grinder, followed by removal of the glass beads by filtration, to provide a toluene dispersion. Further, a solution of 5.0 g of polystyrene dissolved in 100 ml of toluene was mixed with the above toluene dispersion to provide a coating solution for a second receptor layer.

(b) A xylene solution was prepared by adding 13 g of a styrene-glycidyl methacrylate copolymer [copolymeric ratio 9:1 (weight ratio)] and 9 g of Triton X-100 to 300 ml of xylene, and then 91 g of a powdery filter paper C was added to the solution and the resultant mixture was stirred well to provide a coating solution for spreading layer.

B. Preparation of analytical element:

On a transport polyethyleneterephthalate support applied with subbing of a film thickness of about 180 microns, the layers having the following compositions were successively coated by use of the above coating solutions ($a_1$), ($a_2$) and (b) to prepare an analytical element—3 of this invention.

($A_1$) First receptor layer: A layer containing the following:

| | |
|---|---|
| Gelatin | 25 g/m² |
| NBT | 820 mg/m² |
| NAD+ | 3.8 g/m² |
| Lithium lactate | 10 g/m² |
| Tris-hydroxymethylaminomethane | 3.9 g/m² |
| HCl-Tris-hydroxymethylaminomethane | 2.3 g/m² |
| Triton X-100 | 0.5 g/m² |
| 1,2-bis(vinylsulfonyl)thane | 0.4 g/m² |

(b) Spreading layer: A layer containing the following:

| | |
|---|---|
| Powdery filter paper C | 91 g/m² |
| Styrene-glycidylmethacrylate (9:1) copolymer | 13 g/m² |

-continued

| | |
|---|---|
| Triton X-100 | 9 g/m² |

(4) Preparation of Analytical element—4 of this invention

A. Preparation of coating solutions ($a_1$) In 150 ml of distilled water were dissolved 25 g of gelatin, 820 mg of NBT, 3.8 g of NAD+, 0.5 g of Triton X-100, 10 g of lithium lactate, 0.2 g of 1,2-bis(vinylsulfonyl)ethane, to provide a coating solution for a first receptor layer.

($a_2$) A liquid of 50 ml of n-butanol to which 3.9 g of Tris-hydroxymethylaminomethane and 2.3 g of HCl-Tris-hydroxymethylaminomethane were added was dispersed into minute particles with addition of 35 ml of glass beads by means of a sand grinder, followed by removal of the glass beads by filtration. This dispersion was added into a solution of 5 g of polyvinyl pyrrolidone dissolved in 50 ml of n-butanol and mixed therewith to provide a coating solution for a second receptor layer.

(b) To 50 ml of xylene was added 52 mg of N-methylphenazine methosulfate (PMS), and the mixture was dispersed in minute particles in xylene with addition of 70 ml of glass beads by means of a sand grinder, followed by removal of the glass beads by filtration, to provide each xylene dispersion. Further, a xylene solution of 13 g of a styrene-glycidyl methacrylate copolymer [copolymeric ratio: 9 : 1 (weight ratio)]and 9 g of Triton X - 100 dissolved in 300 ml of xylene was prepared, and mixed with the xylene dispersion. Into the resultant mixture was added 91 g of a powdery filter paper C [produced by Toyo Roshi Co., 300 mesh or finer], followed by thorough stirring, to provide a coating solution for spreading layer.

B. Preparation of analytical element

On a transparent polyethyleneterephthalate support applied with subbing of a film thickness of about 180 microns, the layers having the following compositions were successively coated by use of the above coating solutions ($a_1$), ($a_2$) and (b) to prepare an analytical element—4 of this invention, ($a_1$) First receptor layer: A layer containing the following:

| | |
|---|---|
| Gelatin | 25 g/m² |
| NAD+ | 3.8 g/m² |
| NBT | 820 mg/m² |
| Lithium lactate | 10 g/m² |
| Triton X-100 | 0.5 g/m² |
| 1,2-bis(vinylsulfonyl)ethane | 0.2 g/m² |

($a_2$) Second receptor layer: A layer containing the following:

| | |
|---|---|
| Polyvinyl pyrrolidone | 5 g/m² |
| Tris-hydroxymethylaminomethane | 3.9 g/m² |
| HCl-Tris-hydroxymethylaminomethane | 2.3 g/m² |

(b) Spreading layer: A layer containing the following:

| | |
|---|---|
| Powdery filter paper C | 91 g/m² |

| Styrene-glycidylmethacrylate (9:1) copolymer | 13 g/m² |
|---|---|
| PMS | 52 mg/m² |
| Triton X-100 | 9 g/m² |

(5) Preparation of Analytical element—5 of this invention:

A. Preparation of coating solutions

To 60 g of a gelatin/styrene-glycidylmethacrylate copolymer (weight ratio 95:5) copolymer =7/93 (weight ratio) was added 150 ml of distilled water, and into the resultant mixture were added 820 mg of NBT, 3.8 g of NAD+, 3.9 g of Tris-hydroxymethylaminomethane, 2.3 g of HCl-Trishydroxymethylaminomethane, 10 g of lithium lactate, 1.5 g of Triton X-100 and 0.2 g of 1,2-bis(vinylsulfonyl)ethane, to provide a coating solution for a receptor layer.

The coating solution for spreading layer employed was the same as that employed for the analytical element—4.

B. Preparation of analytical element

On a transparent polyethyleneterephthalate support applied with subbing of a film thickness of about 180 microns, the layers having the following compositions were successively coated by use of the above coating solutions to prepare an analytical element—5 of this invention.

(a) Receptor layer: A layer containing the following:

| Gelatin/styrene-glycidyl methacrylate (95:5) copolymer | 60 g/m² |
|---|---|
| NBT | 820 mg/m² |
| NAD+ | 3.8 g/m² |
| Tris-hydroxymethylaminomethane | 3.9 g/m² |
| HCl-Tris-hydroxymethylaminomethane | 2.3 g/m² |
| Lithium lactate | 10 g/m² |
| Triton X-100 | 1.5 g/m² |
| 1,2-bis(vinylsulfonyl)ethane | 0.2 g/m² |

(b) Spreading layer: A layer containing the following:

| Powdery filter paper C | 91 g/m² |
|---|---|
| Styrene-glycidylmethacrylate (9:1) copolymer | 13 g/m² |
| PMS | 52 mg/m² |
| Triton X-100 | 9 g/m² |

(6) Preparation of comparative analytical element—1

A. Preparation of coating solutions (a₁) In 150 ml of distilled water were dissolved 25 g of gelatin, 68 mg of MeO.PMS, 820 mg of NBT, 5 g of lithium lactate, 3.8 g of NAD+, 3.9 g of Tris-hydroxymethylaminomethane, 2.3 g of HCl-Tris-hydroxymethylaminomethane, 0.2 g of 1,2-bis(vinylsulfonyl)ethane and 0.5 g of Triton X-100 to provide a coating solution for a receptor layer.

The coating solution for spreading layer employed was the same as that employed for the analytical element—2.

B. Preparation of analytical element

On a transparent polyethyleneterephthalate support applied with subbing of a film thickness of about 180 microns, the layers having the following compositions were successively coated by use of the above coating solutions to prepare a comparative analytical element—1.

(a) Receptor layer: A layer containing the following:

| Gelatin | 25 g/m² |
|---|---|
| MeO.PMS | 68 mg/m² |
| NBT | 820 mg/m² |
| Lithium lactate | 5 g/m² |
| NAD+ | 3.8 g/m² |
| Tris-hydroxymethylaminomethane | 3.9 g/m² |
| HCl-Tris-hydroxymethylaminomethane | 2.3 g/m² |
| Triton X-100 | 0.5 g/m² |
| 1,2-bis(vinylsulfonyl)ethane | 0.2 g/m² |

(b) Spreading layer: A layer containing the following:

| Powder filter paper C | 91 g/m² |
|---|---|
| Styrene-glycidylmethacrylate (9:1) copolymer | 13 g/m² |
| Triton X-100 | 9 g/m² |

(7) Preparation of a comparative analytical element—2

In preparation of a coating solution, 15 g of polyvinyl pyrrolidone was used in place of gelatin and 52 mg of PMS in place of MeO.PMS, following otherwise the same procedure as in preparation of the comparative analytical element—1, to prepare a comparative analytical element—2.

(8) Preparation of comparative analytical element—3

A. Preparation of coating solutions

To 60 g of a gelatin/styrene-glycidyl- methacrylate copolymer (weight ratio 95:5) copolymer =7/93 (weight ratio) (polymer particles as disclosed in Japanese Provisional Patent Publication No.70163/1983) was added 150 ml of distilled water, and into the resultant mixture were added 72 mg of MeO PMS, 820 mg of NBT, 3.8 g of NAD+, 3.9 g of Tris-hydroxymethylaminomethane, 2.3 g of HCl-Tris-hydroxymethylaminomethane, 10 g of lithium lactate, 1.5 g of Triton X-100 and 0.2 g of 1,2-bis(vinylsulfonyl)ethane, to provide a coating solution for a receptor layer.

The coating solution for spreading layer employed was the same as that employed for the analytical element—2.

B. Preparation of analytical element

On a transparent polyethyleneterephthalate support applied with subbing of a film thickness of about 180 microns, the layers having the following compositions were successively coated by use of the above coating solutions to prepare a comparative analytical element—3.

(a) Receptor layer: A layer containing the following:

| Gelatin/styrene-glycidyl methacrylate (95:5) copolymer | 60 g/m² |
|---|---|
| MeO.PMS | 72 mg/m² |
| NBT | 820 mg/m² |
| NAD+ | 3.8 g/m² |
| Tris-hydroxymethylaminomethane | 3.9 g/m² |
| HCl-Tris-hydroxymethylaminomethane | 2.3 g/m² |
| Lithium lactate | 10 g/m² |

-continued

| | |
|---|---|
| Triton X-100 | 1.5 g/m² |
| 1,2-bis(vinylsulfonyl)ethane | 0.2 g/m² |

(b) Spreading layer: A layer containing the following:

| | |
|---|---|
| Powdery filter paper C | 91 g/m² |
| Styrene-glycidylmethacrylate (9:1) copolymer | 10 g/m² |
| Triton X-100 | 9 g/m² |

The thus prepared analytical elements 1 to 5 of this invention and comparative analytical elements 1 to 3 were subjected to measurements of reflected densities (fog) from the support side by use of a filter with λmax of 580 nm, immediately after preparation and after storage at 35° C. for 3 days. The results are shown in Table 1.

TABLE 1

| | Fog (reflected density) | |
|---|---|---|
| | On the same day | After 3 days' storage |
| Analytical element of Invention - 1 | 0.22 | 0.43 |
| Analytical element of Invention - 2 | 0.23 | 0.45 |
| Analytical element of Invention - 3 | 0.24 | 0.45 |
| Analytical element of Invention - 4 | 0.21 | 0.38 |
| Analytical element of Invention - 5 | 0.23 | 0.44 |
| Comparative analytical element - 1 | 0.78 | 1.32 |
| Comparative analytical element - 2 | 0.81 | 1.31 |
| Comparative analytical element - 3 | 0.80 | 1.33 |

As apparently seen from Table 1, the analytical elements of this invention are very low in fog density on the same day and after storage for 3 days to be improved in stability of the element, as compared with comparative analytical elements.

EXAMPLE 2

From the receptor layers (1–12) and the spreading layers (1–12) with the compositions as shown in Table 2 and Table 3 (coated quantities in coated layers), the combinations of the receptor layer and the spreading layer as shown in Table 4 were suitably chosen and provided by coating to prepare the analytical elements of this invention (6–16) and comparative analytical elements (4–8). Then, the reflected densities for the respective analytical elements were measured to obtain the results as shown in Table 4.

TABLE 2

| | Receptor layer composition | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Lithium lactate (g/m²) | 7.5 | 10 | — | — | 7.5 | — | 5 | — | — | — | 7.5 | — |
| 1-Methoxy-N-methylphenazine-methosulfate (mg/m²) | 68 | — | 72 | — | — | — | — | — | — | 68 | — | — |
| N-methylphenazinemetho-sulfate (mg/m²) | — | 52 | — | — | — | — | — | — | — | — | — | 52 |
| Oxidation type nicotinamide adenine dinucleotide (g/m²) | 3.8 | — | — | — | — | — | — | — | — | 3.8 | — | — |
| 3,3'-(3,3'-Dimethoxy-4,4'-biphenylene)-bis[2-(p-nitrophenyl)-5-phenyltetrazolium chloride] (NBT) (mg/m²) | — | 820 | — | 820 | — | — | — | — | — | — | 820 | — |
| 1,2-Bis(vinylsulfonyl)-ethane (g/m²) | — | 0.2 | — | — | — | — | — | — | — | — | 0.4 | 0.2 |
| p-Octylphenoxy polyethoxy-ethanol (g/m²) | 0.5 | — | 0.2 | — | — | — | — | — | — | — | 0.5 | — |
| Trishydroxymethylamino methane (g/m²) | 3.9 | — | — | — | — | — | — | — | — | 3.9 | — | — |
| HCl-Tris-hydroxymethylamino-methane (g/m²) | 2.3 | — | — | — | — | — | — | — | — | 2.3 | — | — |
| Gelatin (g/m²) | — | 25 | — | — | — | — | — | — | — | — | 25 | — |
| Polyvinyl pyrrolidone (g/m²) | — | — | — | — | — | — | 15 | — | — | — | — | — |
| Polyacrylamide (g/m²) | — | — | — | — | — | 12.5 | — | — | — | — | 12.5 | — |
| Gelatin/styrene-glycidyl methacrylate copolymer*¹ (g/m²) | 50 | — | — | — | — | — | — | — | — | — | — | 50 |

TABLE 3

| | Spreading layer composition | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Powdery filter paper C*² (g/m²) | | 91 | | 46 | 91 | 45 | | 91 | | | | — |
| Styrene-glycidylmethacrylate (weight ratio 9:1) copolymer (g/m²) | | 13 | | 7 | 13 | 6 | | 13 | | | | — |
| p-Octylphenoxy polyethoxy-ethanol (g/m²) | | 9 | | 5 | 9 | 4 | | 9 | | | | — |
| Titanium dioxide (g/m²) | | | | | | | | | | 30 | | |
| Cellulose diacetate (g/m²) | | | | | | | | | | 3.7 | | |
| 1-Methoxy-N-methylphenazine-methosulfate (mg/m²) | — | 72 | — | | 72 | — | 72 | — | 72 | — | 72 | — |
| Oxidation type nicotinamide adenine dinucleotide (g/m²) | — | | 3.8 | — | | 3.8 | — | 3.8 | — | | | |

TABLE 3-continued

| | Spreading layer composition | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Lithium lactate (g/m$^2$) | | | | | — | | | | 10 | | — | |
| 3,3'-(3,3'-Dimethoxy-4,4'-biphenylene)-bis[2-(p-nitrophenyl)-5-phenyltetrazolium chloride] (NBT) (mg/m$^2$) | 820 | | | — | | | 820 | | — | 820 | | — |

The coating solutions for receptor layers 7, 8 and 9 were directly dispersed by means of a sand grinder in a solvent of n-butanol. Other coating solutions were provided as aqueous solutions.
*[1] Polymer of Gelatin/styrene-glycidyl methacrylate (weight ratio 95:5) copolymer = 2/98 as disclosed in Japanese Provisional Patent Publication No. 70163/1983)
*[2] produced by Toyo Roshi Co., 300 mesh or finer.

TABLE 4

| | Receptor layer | | Spreading layer | | Reflected density(fog) | |
|---|---|---|---|---|---|---|
| | First layer | Second layer | First layer | Second layer | Same day | 3 days' storage |
| Analytical element of invention - 6 | Receptor layer - 1 | — | Spreading layer - 1 | — | 0.24 | 0.45 |
| Analytical element of invention - 7 | Receptor layer - 2 | — | Spreading layer - 1 | — | 0.22 | 0.42 |
| Analytical element of invention - 8 | Receptor layer - 3 | — | Spreading layer - 2 | — | 0.20 | 0.42 |
| Analytical element of invention - 9 | Receptor layer - 1 | — | Spreading layer - 10 | — | 0.25 | 0.44 |
| Analytical element of invention - 10 | Receptor layer - 2 | — | Spreading layer - 10 | — | 0.20 | 0.45 |
| Analytical element of invention - 11 | Receptor layer - 3 | — | Spreading layer - 11 | — | 0.21 | 0.43 |
| Analytical element of invention - 12 | Receptor layer - 4 | Receptor layer - 8 | Spreading layer - 4 | — | 0.19 | 0.37 |
| Analytical element of invention - 13 | Receptor layer - 5 | Receptor layer - 7 | Spreading layer - 9 | — | 0.23 | 0.43 |
| Analytical element of invention - 14 | Receptor layer - 6 | — | Spreading layer - 7 | Spreading layer - 5 | 0.21 | 0.43 |
| Analytical element of invention - 15 | Receptor layer - 9 | — | Spreading layer - 8 | — | 0.21 | 0.42 |
| Analytical element of invention - 16 | Receptor layer - 4 | Receptor layer - 9 | Spreading layer - 6 | — | 0.20 | 0.39 |
| Comparative analytical element - 4 | Receptor layer - 11 | — | Spreading layer - 3 | — | 0.80 | 1.30 |
| Comparative analytical element - 5 | Receptor layer - 12 | — | Spreading layer - 3 | — | 0.80 | 1.33 |
| Comparative analytical element - 6 | Receptor layer - 10 | — | Spreading layer - 12 | — | 0.81 | 1.31 |
| Comparative analytical element - 7 | Receptor layer - 11 | — | Spreading layer - 12 | — | 0.84 | 1.35 |
| Comparative analytical element - 8 | Receptor layer - 12 | — | Spreading layer - 12 | — | 0.83 | 1.38 |

As apparently seen from Table 4, as compared with the comparative analytical elements, the analytical elements of this invention are all lower in fog density on the same day and after storage for 3 days, thus indicating improvement in stability of the element.

EXAMPLE 3

For each of the analytical elements 1, 4, 5, 8, 12, 14 and the comparative analytical elements 1, 2, 3 and 8, prepared in Example 1 and Example 2, both immediately after preparation and after stored at 35° C. for 3 days, each 10 μl of standard sera having an LDH activity of 126 Wroblewsky units, 253 Wroblewsky units and 506 Wroblewsky units as confirmed by Unikit ® Rate (produced by Chugai Pharmaceutical Co.) was added dropwise onto the spreading layer, and after incubation at 37° C. for 10 minutes, the reflected density was measured from the support side by use of a filter with λ max of 580 nm. The results are shown in Table 5.

TABLE 5

| LDH activity | Reflected density | | | | | |
|---|---|---|---|---|---|---|
| | On the same day | | | After 3 days' storage | | |
| (Wroblewsky units) | 126 | 253 | 506 | 126 | 253 | 506 |
| Analytical element of Invention - 1 | 0.42 | 0.68 | 0.95 | 0.56 | 0.81 | 1.05 |
| Analytical element of Invention - 4 | 0.40 | 0.63 | 0.85 | 0.55 | 0.82 | 1.06 |
| Analytical element of Invention - 5 | 0.44 | 0.70 | 0.96 | 0.57 | 0.82 | 1.07 |
| Analytical element of Invention - 8 | 0.41 | 0.66 | 0.93 | 0.57 | 0.83 | 1.06 |
| Analytical element of Invention - 12 | 0.42 | 0.69 | 0.95 | 0.52 | 0.79 | 1.02 |
| Analytical element of Invention - 14 | 0.40 | 0.69 | 0.94 | 0.58 | 0.83 | 1.07 |
| Comparative analytical element - 1 | 0.85 | 0.91 | 1.01 | 1.34 | 1.35 | 1.33 |
| Comparative analytical element - 2 | 0.88 | 0.95 | 1.04 | 1.31 | 1.31 | 1.34 |
| Comparative analytical element - 3 | 0.87 | 0.93 | 1.03 | 1.33 | 1.35 | 1.32 |
| Comparative analytical element - 8 | 0.89 | 0.96 | 1.07 | 1.36 | 1.37 | 1.38 |

As apparently seen from the results in Table 5, as contrasted to the changes in coloration desnsities which are very low corresponding to the changes in LDH activities in comparative analytical elements, coloration density changes with good rise-up are exhibited in the analytical elements of this invention, exhibiting also good coloration density changes corresponding to the changes in LDH activity even after storage at 35° C. for 3 days.

EXAMPLE 4

In the analytical elements 1-16 of this invention and the comparative analytical elements 1-8, in place of lithium lactate, 467 mg/m$^2$ of α-keto glutaric acid, 21.3 g/m$^2$ of aspartic acid and 1200 units/m$_2$ of glutamate dehydrogenase were added, and 5.9 g/m$^2$ of dipotassium monohydrogen phosphate and 2.2 g/m$^2$ of monopotassium dihydrogen phosphate were added as buffering agents in place of Tris-hydroxymethylaminomethane and hydrochloride thereof, to prepare the analytical elements according to this invention for GOT (17-32) and comparative analytical elements for GOT (9-16).

For each of the analytical elements thus obtained, color forming characteristics and fog densities were measured according to the same procedure as in Example 3 and Example 1. As the result, comparative analytical elements were high in fog and markedly small in coloration density change. Also, after storage at 35° C. for 3 days, the comparative analytical elements were high in fog, whereby even discrimination whether the color formed density was due to dropwise addition of serum was difficult. On the other hand, the analytical elements of this invention were low in fog density even after storage, exhibiting good colorations corresponding to GOT activities.

EXAMPLE 5

In the analytical elements 1-16 of this invention and the comparative analytical elements 1-8, in place of lithium lactate, 467 mg/m$^2$ of α-keto glutaric acid, 28.5 g/m$^2$ of alanine and 1200 units/m$^2$ of glutamate dehydrogenase were added, and the same buffering agents as in Example 4 were added, to prepare the analytical elements according to this invention for GPT (33-48) and comparative analytical elements (17-24).

For each of the analytical elements thus obtained color forming characteristics and fog densities were measured according to the same procedure as in Example 3 and Example 1. As the result, comparative analytical elements were high in fog and markedly small ir coloration density change. Also, after storage at 35° C for 3 days, the comparative analytical elements were high in fog, whereby even discrimination whether the color formed density was due to dropwise addition of serum was difficult. On the other hand, the analytical elements of this invention were low in fog density ever after storage, exhibiting good colorations corresponding to GPT activities.

EXAMPLE 6

In the analytical elements 1-16 of this invention and the comparative analytical elements 1-8, in place of lithium lactate, 15.0 g/m$^2$ of disodium creatinephosphate, 2.3 g/m$^2$ of sodium adenosine-5'-2-phosphate, 4.1 g/m$_2$ of glucose, 20 g/m$^2$ of magnesium sulfate hydrate. 1.5 g/m$^2$ of NADP$^+$, 100 mg/m$^2$ of hexokinase and 20 mg/m$^2$ of glucose-6-phosphate dehydrogenase were added, and 2.7 g of Tris-hydroxymethylaminomethane and 3.5 g/m$^2$ of hydrochloride thereof were added as buffering agents, to prepare the analytical elements according to this invention for CPK (49-64) and comparative analytical elements (25-32).

For each of the analytical elements thus obtained, color forming characteristics and fog densities were measured according to the same procedure as in Example 3 and Example 1. As the result, comparative analytical elements were high in fog and markedly small in coloration density change. Also, after storage at 35° C. for 3 days, the comparative analytical elements were high in fog, whereby even discrimination whether the color formed density was due to dropwise addition of serum was difficult. On the other hand, the analytical elements of this invention were low in fog density even after storage, exhibiting good colorations corresponding to CPK activities.

We claim:

1. A dry multilayer analytical element for analysis of an enzyme or triglycerides in a fluid sample comprising:
   a support which is impervious to liquids and is light transmissive,
   a first layer on said support, said first layer comprising a dye forming precursor which is a tetrazolium salt selected from the group consisting of 3,3'-(3,3'-dimethoxy-4,4'-biphenylene)-bis [2-(p-nitrophenyl)-5-phenyltetrazolium chloride] (NBT), 3,3'-(3,3'-dimethoxy-4, 4'-biphenylene)-bis[2,5-diphenyltetrazolium chloride] (BT), 3-(4',5'-dimethyltriazolyl-2)-2,4-diphenyltetrazolium bromide (MTT), 2-(p-iodophenyl)-3-(p-nitrophenyl)-5-phenyl-tetrazolium chloride (INT), 2,2',5,5'-tetra-(p-nitrophenyl)-3,3'-(3-dimethoxy-4-diphenylene)-ditetrazolium chloride (TNBT), 2,3,5-triphenyltetrazolium chloride (TT) and 3,3'-(4,4'-biphenylene)-bis [2,5-diphenyltetrazolium chloride] (NT), and
   a second layer provided adjacent to said first layer, said second layer comprising an electron-transmitting agent selected from the group consisting of N-methylphenazine methosulfates, meldra Blue, Methylene Blue and diaphorase,
   wherein:

one of said first layer and said second layer comprises an oxidation co-enzyme, and one of said first layer and said second layer comprises a reagent comprising an enzyme substrate, enzyme or coenzyme other than an oxidation coenzyme, and said oxidation co-enzyme is oxidized nicotinamide adenine dinucleotide (NAD+) or oxidized nicotinamide adenine dinucleotide phosphoric acid (NADP+); and said reagent is operable to react with said oxidation co-enzyme to form a reduction co-enzyme, in the presence of said enzyme or said triglycerides in said fluid sample, whereby said reduction co-enzyme reduces said electron-transmitting agent to produce a reduced electron-transmitting agent and said reduced electron-transmitting agent reduces said tetrazolium salt to form a dye which can be detected and measured.

2. The analytical element according to claim 1 wherein the first layer comprises a binder composed of a gelatin derivative.

3. The analytical element according to claim 1, wherein the first layer comprises a hydrophobic binder.

4. The analytical element according to claim 1 wherein a void volume of the second layer is about 20 to about 85%.

5. The analytical element of claim 1, wherein said first layer is a receptor layer where the dye is formed, detected and measured.

6. The analytical element according to claim 5, wherein the receptor layer contains a non-ionic surfactant.

7. The analytical element according to claim 1, wherein the contents of the electron transmitting agent, the dye-forming precursor, the oxidation coenzyme, and the reagent are 1 mg/m² to 1 g/m², 10 mg/m² to 10 g/m² to 50 g/m² and 10 mg/m² to 100 g/m², respectively.

8. The analytical element according to claim 1, wherein said enzyme is lactage dehydrogenase and said reagent is lactic acid.

9. The analytical element according to claim 8, wherein
said electron transmitting agent is in an amount of from 10 to 500 mg/m²; said dye-forming precursor is in an amount of from 50 mg/m² to 3 g/m²; said oxidation co-enzyme is in an amount of from 50 mg/m²; and said reagent is in an amount from 10 mg/m² to 100 g/m².

10. The analytical element according to claim 9, wherein the first layer comprises a hydrophobic binder.

11. The analytical element according to claim 11 wherein said enzyme is glutamate-oxaloacetate transaminase and said reagent is selected from the group consisting of and said reagent is selected from the group consisting of aspartic acid, alpha-ketoglutaric acid and glutamate dehydrogenase.

12. The analytical element according to claim 11, wherein
said electron transmitting agent is in an amount of from 10 to 500 mg/m²; said dye-forming precursor is in an amount of from 50 mg/m² to 3 g/m²; said oxidation co-enzyme is in an amount of from 50 mg/m²; and said reagent is in an amount from 10 mg/m² to 100 g/m².

13. The analytical element according to claim 12, wherein the first layer comprises a hydrophobic binder.

14. The analytical element according to claim wherein said enzyme is glutamate-pyruvate transminas and said reagent is selected from the group consisting of alanine, alpha-ketoglutaric acid and glutamate dehydro genase.

15. The analytical element according to claim 1 wherein
said electron transmitting agent is in an amount of from 10 to 500 mg/m²; said dye-forming precurso is in an amount of from 50 mg/m² to 3 g/m²; sai oxidation co-enzyme is in an amount of from 5 mg/m²; and said reagent is in an amount from 1 mg/m² to 100 g/m².

16. The analytical element according to claim 1 wherein the first layer comprises a hydrophobic binde 17. The analytical element according to claim 1] wherein said enzyme is amylase and said reagent i selected form the group consisting of maltopentose orthophospharic acid, beta-phosphoglucomutase, glu cose oxidase and maltose phosphorylase.

18. The analytical element according to claim 1" wherein
said electron transmitting agent is in an amount c from 10 to 500 mg/m²; said dye-forming precurso is an amount of from 50 mg/m² to 3 g/m²; sai oxidation co-enzyme is in an amount of from 5 mg/m²; and said reagent is in an amount from 1 mg/m² to 100 g/m².

19. The analytical element according to claim 18 wherein the first layer comprises a hydrophobic binde 20. The analytical element according to claim 11 wherein said enzyme is creatine phosphokinase and sai reagent is selected from the group consisting of cre atine, adenosine triphosphoric acid, hexokinase an glucose-6-phosphate dehydrogenase.

21. The analytical element according to claim 20 wherein
said electron transmitting agent is in an amount o from 10 to 500 mg/m²; said dye-forming precurso is in an amount of from 50 mg/m² to 3 g/m²; sai oxidation co-enzyme is in an amount of from 5 mg/m²; and said reagent is in an amount from 1 mg/m² to 100 g/m².

22. The analytical element according to claim 21 wherein the first layer comprises a hydrophobic com prises a hydrophobic binder.

23. The analytical element according to claim 1 wherein a triglyceride is analyzed and said reagent i selected from the group consisting of lipoprotein lipase glycerokinase, glycerophosphate dehydrogenase an adenosine triphosphoric acid.

24. The analytical element according to claim 23 wherein
said electron transmitting agent is in an amount o from 10 to 500 mg/m²; said dye-forming precurso is in an amount of from 50 mg/m² to 3 g/m²; sai oxidation co-enzyme is in an amount of from 5 mg/m²; and said reagent is in an amount from 1 mg/m² to 100 gm².

25. The analytical element of claim 24, wherein th first layer comprises a hydrophobic binder.

26. The analytical element according to claim 11 wherein the electron transmitting agent and the dy forming precursor are in the form of fine particles.

27. The analytical element of claim 5, wherein sai second layer is a spreading layer made of a fibrous po rous material that functions to distribute a constan volume of fluid sample, to remove interfering sub stances and/or to effect background action which reflects measured light transmitted through the support.

28. The analytical element of claim 11 wherein said second layer is a spreading layer made of a fibrous porous material that functions to distribute a constant volume of fluid sample, to remove interfering substances and/or to effect background action which reflects measured light transmitted through the support.

* * * * *